(12) United States Patent
Yao et al.

(10) Patent No.: US 10,071,846 B2
(45) Date of Patent: Sep. 11, 2018

(54) TEST-STRIP STORAGE VIAL

(71) Applicant: Sinocare Inc., Changsha, Hunan (CN)

(72) Inventors: Nianlong Yao, Hunan (CN); Feng Hu, Hunan (CN); Xiaohua Cai, Hunan (CN)

(73) Assignee: Sinocare Inc. (CN)

( * ) Notice: Subject to any disclaimer, the term of this patent is extended or adjusted under 35 U.S.C. 154(b) by 0 days.

(21) Appl. No.: 15/211,930

(22) Filed: Jul. 15, 2016

(65) Prior Publication Data

US 2017/0166387 A1    Jun. 15, 2017

(30) Foreign Application Priority Data

Dec. 10, 2015    (CN) .......................... 2015 2 1021016

(51) Int. Cl.
  *B65H 3/00* (2006.01)
  *B65D 83/08* (2006.01)
  *G01N 33/487* (2006.01)

(52) U.S. Cl.
  CPC ... *B65D 83/0829* (2013.01); *G01N 33/48757* (2013.01); *G01N 33/48778* (2013.01)

(58) Field of Classification Search
  CPC ......... B65D 83/0829; G01N 33/48757; G01N 33/48778
  USPC ........................................................ 221/270
  See application file for complete search history.

(56) References Cited

U.S. PATENT DOCUMENTS

| | | | | |
|---|---|---|---|---|
| 3,393,831 A | * | 7/1968 | Stewart .................... | A47F 1/06 221/232 |
| 5,178,298 A | * | 1/1993 | Allina .................. | B65D 83/0418 206/457 |
| 5,975,349 A | * | 11/1999 | Menes ..................... | B65H 1/06 221/232 |
| 6,997,343 B2 | * | 2/2006 | May ......................... | B65H 1/00 221/232 |
| 7,677,409 B2 | * | 3/2010 | Reynolds ........... | A61B 5/14532 221/208 |
| 7,857,165 B2 | * | 12/2010 | Matsumoto ............ | G01D 11/24 221/197 |
| 7,935,307 B2 | * | 5/2011 | Angelides ........ | G01N 33/48757 422/401 |
| 8,523,011 B2 | * | 9/2013 | Haas .................. | B65D 83/0418 206/540 |

(Continued)

FOREIGN PATENT DOCUMENTS

WO    WO 03082092 A1 * 10/2003 ....... G01N 33/48757

*Primary Examiner* — Rakesh Kumar

(57) ABSTRACT

The present invention relates to a test-strip storage vial, comprising a vial body, a storing chamber for storing test strips, a push button, and a top-lifted unit; wherein the push button is located at one end of the storing chamber; wherein a top-lifted unit is located at another end of the storing chamber; wherein the push button slides horizontal to remove test strips the storing chamber; wherein the top-lifted unit supports the test strips and lifts the test strips in a vertical direction; wherein the vial body further comprising an upper cover and lower vial body, wherein the lower vial body is detachably connected to the upper cover; wherein the push button is glidingly connected with the upper cover, wherein the top-lifted unit is located in the lower vial body; wherein a push button spring provides horizontal tensile force is disposed between the upper cover and the push button.

5 Claims, 3 Drawing Sheets

(56) References Cited

U.S. PATENT DOCUMENTS

| | | | |
|---|---|---|---|
| 9,204,829 B2* | 12/2015 | Prais | G01N 33/48757 |
| 9,383,333 B2* | 7/2016 | Reynolds | G01N 33/48757 |
| 2004/0007585 A1* | 1/2004 | Griffith | G01N 33/48757 |
| | | | 221/232 |
| 2006/0118435 A1* | 6/2006 | Cronin | B65D 47/243 |
| | | | 206/219 |
| 2008/0302814 A9* | 12/2008 | Fenton | A61F 5/08 |
| | | | 221/231 |
| 2015/0160186 A1* | 6/2015 | Garner-Richards | |
| | | | G01N 33/48757 |
| | | | 221/270 |

* cited by examiner

TEST-STRIP STORAGE VIAL

FIELD OF INVENTION

The present invention relates to the field of storage devices, and more particularly, to a test-strip storage vial.

BACKGROUND

In biological and chemical fields, test strips are frequently used in the process of experimentation and testing. Additionally, test strips are also needed in medical testing procedures. The accessibility of test strips is crucial in all the process.

Most common test-strip storage vial is a plastic bottle with ordinary screw cap. When accessing the test strip, people have to unscrew the bottle cap then take out the test strip. The bottle cap must be fastened quickly after use to avoid exposure to moisture causing the failure of the test strips.

The repeated operation of opening and closing the bottle cap can also reduce the efficiency of the testing process. Meanwhile, the test strips in the bottle can be affected by the moisture in the surrounding environment and fail to function normally. When the storage device is used for testing the blood glucose, the first step is to prick a finger using a blood taking needle, then collect a blood sample using the test strip. Under such circumstance, the user can only access the test strip with only one hand. As a result, it's very inconvenient to open the bottle cap. Additionally, the test strip may be contaminated by the sweat or other impurities on user's hand thus producing inaccurate test results Accordingly, accessing the test strip by using hands is not ideal, and using a conventional screw-cap plastic bottle can be inconvenient.

In conclusion, the inconvenience of accessing and high risk of contamination of test strips are urgent problems need to be solved for those skilled in this field.

SUMMARY OF THE INVENTION

The present invention provides a test-strip storage vial with a structure design that can effectively solve the issues relating to inconvenience of accessing and contamination by moisture in the air and impurities on user's hand.

A test-strip storage vial, comprising a vial body, a storing chamber for storing test strips, a push button, and a top-lifted unit; wherein the push button is located at one end of the storing chamber; wherein a top-lifted unit is located at another end of the storing chamber; wherein the push button slides horizontal to remove test strips the storing chamber; wherein the top-lifted unit supports the test strips and lifts the test strips in a vertical direction.

In one embodiment, the vial body further comprises an upper cover and lower vial body, wherein the lower vial body is detachably connected to the upper cover; wherein the push button is glidingly connected with the upper cover, and wherein the top-lifted unit is located in the lower vial body 3.

In another embodiment, a push button spring used for providing horizontal tensile force is disposed between the upper cover and the push button; wherein the upper surface of the push button further comprises a plurality of protruding parts.

In another embodiment, the push button further comprises a push plate.

In another embodiment, the lower vial body 3 further comprises an inner cover, wherein the inner cover further comprising a sliding chute coupled with the push plate; wherein the push plate slides through the sliding chute horizontally, wherein the push plate extends vertically into the storing chamber through the sliding chute.

In another embodiment, the inner cover further comprises a tightly-compressing protruded part, wherein the tightly-compressing protruded part contacts the test strips, wherein the bottom surface of the push plate is lower than that of the tightly-compressing protruded part.

In another embodiment, the inner cover further comprises a guiding chute, and wherein and the top-lifted unit slides vertical along the guiding chute.

In another embodiment, the top-lifted unit further comprises a top-lifted block and a plurality of top-lifted springs; wherein the top-lifted springs are disposed between the top-lifted block and the vial body.

In another embodiment, the top-lifted block further comprises supporting legs, where in the supporting legs are coupled with top-lifted springs; wherein the vial body further comprise a plurality of connecting poles with recess holes; wherein the supporting legs and top-lifted springs are disposed in the recess holes of the connecting poles.

In another embodiment, the top-lifted block further comprises a recess hole for storing drying agent.

BRIEF DESCRIPTION OF THE DRAWINGS

To clearly expound the present invention or the technical solution, the drawings and embodiments are hereinafter combined to illustrate the present invention. Obviously, the drawings are merely some embodiments of the present invention and those skilled in the art can associate themselves with other drawings without paying creative labor.

MARKING INSTRUCTION OF THE DRAWINGS

Upper Cover 1, Inner Cover 2, Lower Vial Body 3, Push Button 4, Protruding Part 5, Push Plate 6, Push Button Spring 7, Tightly-Compressing Protruded Part 8, Test Strip 9, Top-lifted Block 10, Top-lifted Spring 11, Supporting leg 12, Drying Agent 14

DETAILED DESCRIPTION

The present invention provides a test-strip storage vial, which facilitates the accessing of the test strips and prevents the test strips from being contaminated by the surrounding environment.

Drawings and detailed embodiments are combined hereinafter to elaborate the technical principles of the present invention. The description is intended to illustrate, but not to limit the protective scope of the present invention in any way. Based on the detailed description herein, those skilled in the art can associate themselves with other particular embodiments without paying creative labor. Thus, these embodiments shall all fall within the protective scope of the present invention.

Figure 1:
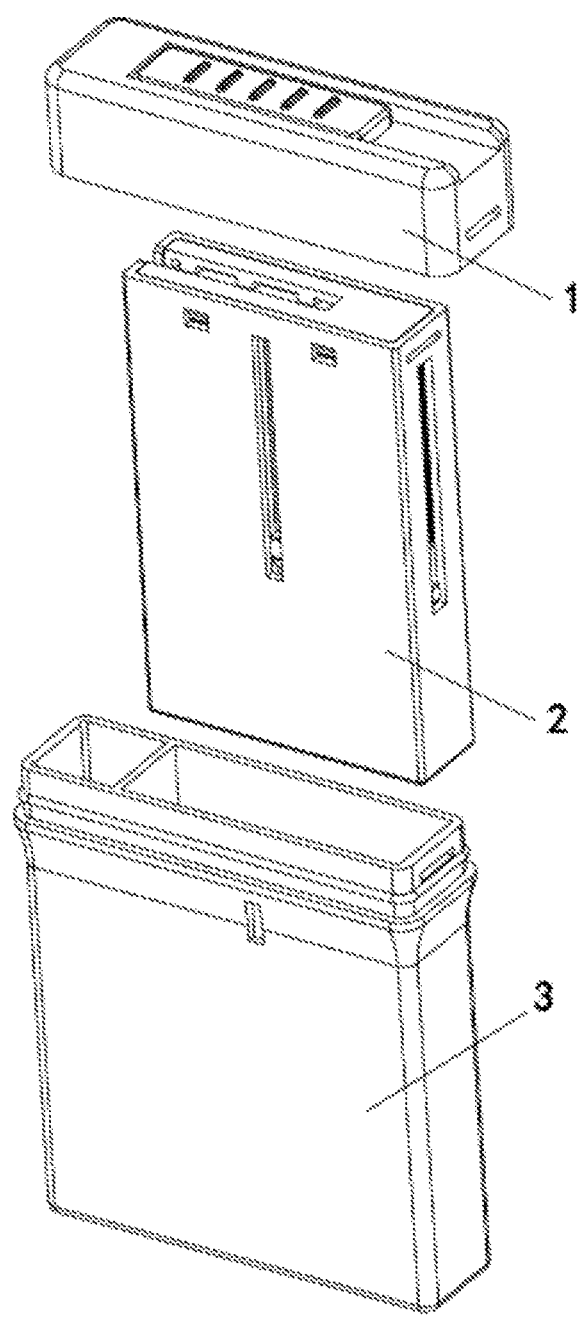
FIG. 1 is external view of the test-strip storage vial in the embodiment of the present invention.
Figure 2:
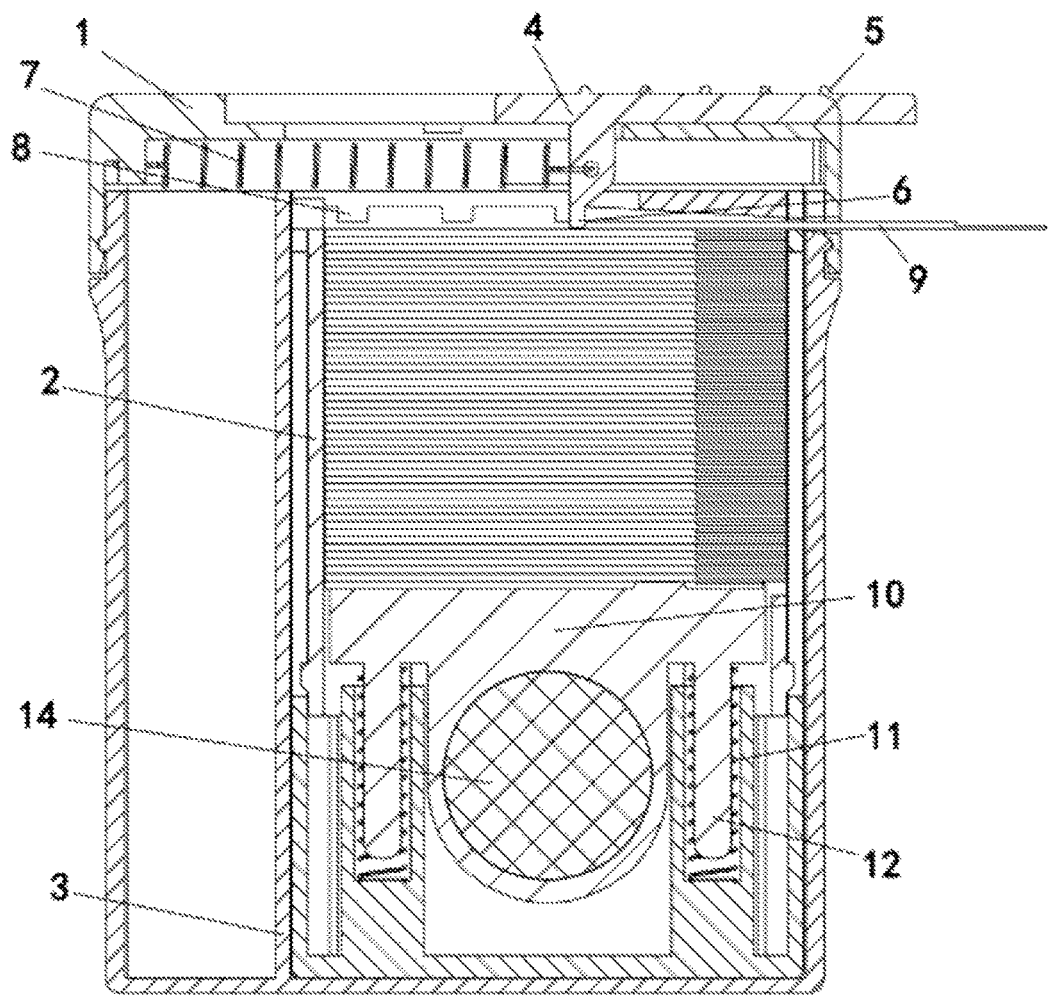
FIG. 2 is al schematic diagram of the structure of the test-strip storage vial in the embodiment of the present invention.

Referring to FIG. 1 and FIG. 2, FIG. 1 is an external view of the test-strip storage vial in the embodiment of the present invention and FIG. 2 is a structural schematic diagram of the test-strip storage vial in the embodiment of the present invention.

The present invention provides a test-strip storage vial, which comprises a vial body and a test-strip 9 storing chamber provided inside of the vial body; the internal shape of the storing chamber is preferred to match the shape of the stacked test-strips 9 so as to prevent the test strips 9 from moving inside of the vial body; the test-strip storage vial also comprises a push button 4 which is provided at one end of the storing chamber, and the push button 4 is preferred to be located on top of the vial body; the test-strip storage vial further comprises a top-lifted unit which is provided at another end of the storing chamber on the vial body, and the top-lifted unit is preferred to be located below the storing chamber; the push button 4 can be used to push the test strips 9 out from the vial body horizontally and the top-lifted unit can be adopted to vertically support the test strips 9 and enable the test strips 9 to move along the direction of the push button 4.

The test-strip storage vial of the present invention has a function of pushing the test strips 9 lifted by the top-lifted unit out from the vial body by pushing the push button 4 connected to a push plate 6, in order for users to insert the test strip 9 into the testing equipment for preparation of a test. The test strip storage vial largely simplifies the process of removing a test strip 9 from ae test-strip storage vial. The user no longer needs to grab a test strip 9 from the depth of the test-strip storage vial instead the process is accomplished by a degree of automation. The entire process of taking out the test strip 9 can be completed by the push plate 6 without touching the strip the hand, thus protecting the test strip 9 from being contaminated by impurities or sweat on the user's hand. Additionally, the test-strip storage vial can prevent the test strips 9 from being exposed to the moisture by limiting the frequent opening and closing of the test strip vial thus prolongs the effective status of the test strips 9. Since the test strip 9 can be taken out just by pushing the push button 4, it achieves convenient single-handed operation by the users.

To optimize the functionality and effectiveness of the present invention, the vial body comprises an upper cover 1 and a lower vial body 3 fixedly connected to the upper cover 1, wherein the lower vial body 3 can be detachable from the upper cover 1. In some embodiments, the connection type is preferred to be a threaded connection with a self-lock structure or other connection types such as buckle connection. The push button 4 is glidingly connected with the upper cover 1 and the top-lifted unit is located in the lower vial body 3. The vial body is preferred to comprise the upper cover 1 and the lower vial body 3 so the vial body can be conveniently opened or close to allow users to supply additional test strips 9 to the storing chamber. After filling the test strips, the upper cover 1 can be closed at any time to protect the test strips 9 from being affected by the moisture in the air in order to prolong the life-span of the test strips 9. The push button 4 is provided on the upper cover 1 and glidingly connected with the upper cover 1.

A push button spring 7 used for providing horizontal tensile force between the upper cover 1 and the push button 4. The upper surface of the push button 4 further comprises protruding parts 5 for increasing friction during operation. During operation, the user pushes the push button 4 in a direction opposite of the tensile force. The push button spring 7 stretches gradually. After the test strips 9 is being delivered from the storing chamber, the user released the push button 4 and the tensile force of the push button spring 7 recovers to its natural position returning the push button to its original position. The push button spring 7 enables the push button 4 to return to its originally position automatically and allows the next test strip to be ready for delivery. The upper surface of the push button 4 are provided with the protruding parts 5 for increasing the friction between the finger and the push button 4. The protruding parts 5 can be multiple small protruding poles perpendicular to the direction in which test strip 9 moves. In one embodiment, push button spring 7 is disposed between the push button 4 and one side of the upper cover. The friction between the finger and the push button 4 needs to be increased so as to prevent the push button 4 from slipping back to its original position under the tensile force of the push button spring 7. The protruding parts 5 can also be in other shapes that can increase the friction between the finger and the push button 4. For example, the protruding parts 5 can be a plurality of small protruding points.

In one embodiment, the push button 4 can further comprise a push plate 6. The push plate 6 is positioned at one side of the storing chamber when the push bottom spring 7 is in its natural state. Preferably, the push plate 6 is vertically extend to the position of the test strips 9

Figure 3:
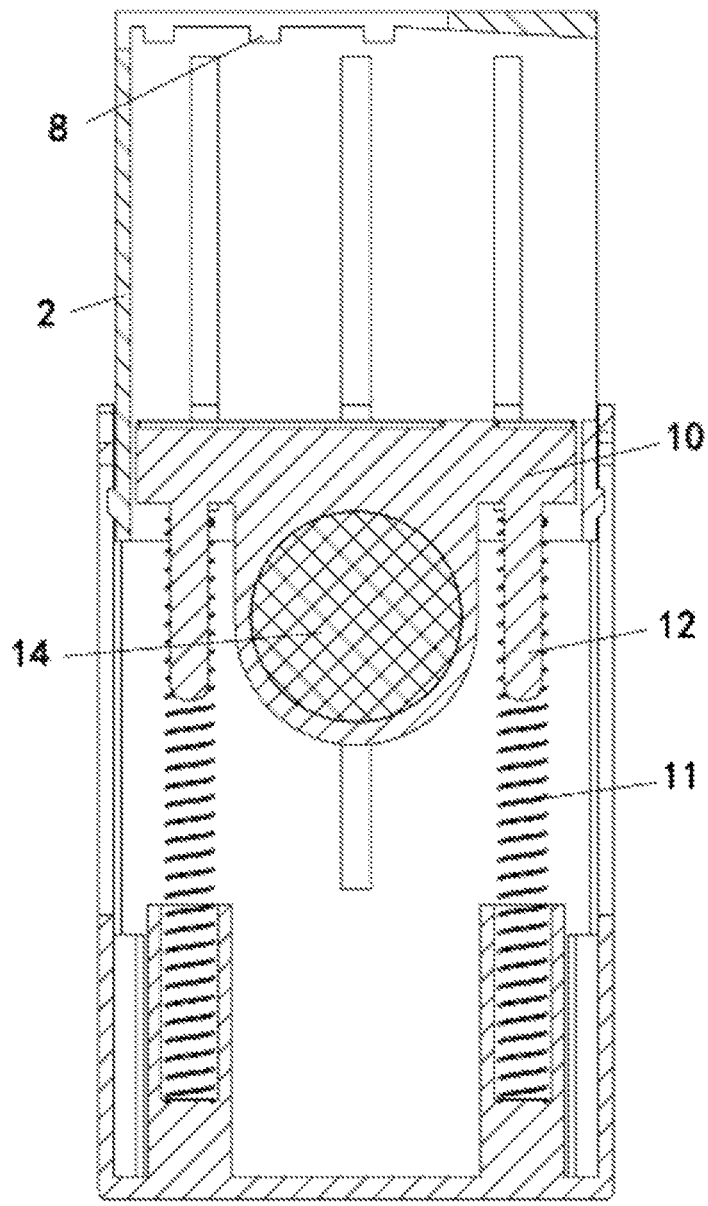
FIG. 3 is a schematic diagram of the structure of the lower vial body in the embodiment of the present invention.

Referring FIG. 3, the lower vial body 3 comprises an inner cover 2, the inner cover 2 further comprising a sliding chute for the push plate 6; the sliding chute allows the push plate 6 to slide horizontally along with the push button 4 and push the test strip 9 out of the storing chamber, wherein the push plate 6 slides protrudes through the sliding chute and extends vertically into the storing chamber; the upper cover 1 comprises a down-pressing unit, which pushes the inner cover 2 tightly. In one embodiment, the inner cover 2 can be removed integrally and the space for storing the test strips 9 can be exposed so that the refilling of the test strips 9 becomes more convenient.

In one embodiment, the inner cover 2 comprises a tightly-compressing protruded part 8 and the bottom surface of the push plate 6 is lower than that of the tightly-compressing protruded part 8. The tightly-compressing protruded part 8 is preferred to be located on the inner top surface of the inner cover 2, wherein there can a plurality of protruded parts 8. The bottom surface of the push plate 6 is lower than that of the tightly-compressing protruded part 8, ensuring the push plate 6 to be in contact with the test strip 9. In this embodiment, the tightly-compressing protruded part 8 maintains the test strips at a certain height. There can be a plurality of tightly-compressing protruded part 8 to keep the test strips 9 uniformly at a horizontal position. The tightly-compressing protruded part 8 can be made in a variety of shapes.

In one embodiment, the inner cover 2 comprises a vertically-directional guiding chute 12. The guiding chute 12 is preferred to be located on the side faces of the inner cover 2. The top-lifted unit slides along the guiding chute. The guiding chute 12 enables the top-lifted unit to be raised and lowered stably inside the inner cover 2 and effectively prevents the test strip 9 from jammed in the passage due to the inclination of the top-lifted unit. The guiding chute also limits the position of the top-lifted unit, inhibiting the top-lifted unit from falling to the bottom or bouncing out of the inner cover 2 to make the assembly and disassembly process and the access to test strip 9 more convenient.

In one embodiment, the top-lifted unit further comprises a top-lifted block 10 and two top-lifted springs 11. The top-lifted springs are disposed between the top-lifted block 10 and the vial body. The test strips 9 are disposed on top of the top-lifted block 10, and the top-lifted springs 11 provides tensile force to push the top-lifted block in the direction away from the bottom of the vial body.

In one embodiment, the top-lifted unit comprises a plurality of supporting legs 12, wherein the number of the plurality of the supporting legs 12 are preferred to be an even number arranged symmetrically according to the shape of the top-lifted unit 10. The supporting legs 12 are disposed inside top-lifted springs 11. The vial body comprises connecting poles with recess holes, wherein the supporting legs 12 and the top-lifted springs 11 are disposed in the recess holes of connecting poles. The supporting legs 12 enables the top-lifted springs 11 to be connected to the top-lifted block 10 in a stable manner and the symmetrically arranged even-numbered supporting legs 12 ensure that the top-lifted block 10 are in a horizontal position without inclination or distortion.

In one embodiment, the top-lifted block 10 further comprises a recess hole for storing the drying agent 14. In this embodiment, drying agent 14 is placed in the recess hole to absorb moisture in the small amount of air in the storage and keeps the test strip 9 in dry state prevent malfunction of the test strips 9 due to dampness.

Each embodiment of the description is illustrated by adopting progressive way and the emphasis of each embodiment is different from the others. The similarity of each embodiment can be cross-referenced.

The description of above embodiments allows those skilled in the art to realize or use the present invention. Without departing from the spirit and essence of the present invention, those skilled in the art can combine, change or modify correspondingly according to the present invention. Therefore, the protective range of the present invention should not be limited to the embodiments above but conform to the widest protective range which is consistent with the principles and innovative characteristics of the present invention.

The invention claimed is:

1. A test-strip storage vial, comprising:
   an upper cover, a lower vial body, and an inner cover, wherein the upper cover and lower vial body are detachably connected, wherein the inner cover is detachably enclosed by the upper cover and lower vial body,
   wherein the inner cover further comprising a storing chamber for storing test strips, and a top-lifted unit;
   wherein the top-lifted unit supports the test strips and lifts the test strips in a vertical direction;
   wherein the upper cover further comprising a push button, a push button spring attached to a side of the upper cover and the push button, wherein a first opening on the upper cover allows the push button to be glidingly connected with the upper cover, wherein the push button slides horizontally to remove test strips from the storing chamber, wherein the push button spring is used for providing horizontal tensile force; wherein an upper surface of the push button further comprises a plurality of protruding parts; wherein the push button further comprises a push plate;
   wherein the upper cover further comprising a second opening, wherein the second opening is aligned with the first opening, wherein the push plate slides through the first opening and second opening horizontally, wherein the push plate extends vertically into the storing chamber through second opening; wherein the inner cover further comprising a tightly-compressing protruded part that is lower than an inner top surface of the inner cover, wherein the tightly-compressing protruded part contacts the test strips, wherein a bottom surface of the push plate is lower than that of the tightly-compressing protruded part.

2. The test-strip storage vial of claim 1, wherein the inner cover further comprising a guiding chute, wherein the guiding chute is detachable connected to the inner cover, and wherein and the top-lifted unit slides vertical along the guiding chute.

3. The test-strip storage vial of claim 1, wherein the top-lifted unit further comprising a top-lifted block and a plurality of top-lifted springs; wherein the top-lifted springs are disposed between the top-lifted block and a bottom of the inner cover.

4. The test-strip storage vial of claim 3, wherein the top-lifted block further comprising a plurality of supporting legs, wherein the supporting legs are coupled with top-lifted springs; wherein the inner cover further comprising a plurality of connecting poles with recess holes; wherein the supporting legs and top-lifted springs are disposed in the recess holes of the connecting poles.

5. The test-strip storage vial of claim 3, wherein the top-lifted block further comprising a recess hole for storing drying agent.

* * * * *